United States Patent [19]

Johannisbauer et al.

[11] Patent Number: 5,480,978
[45] Date of Patent: Jan. 2, 1996

[54] PROCESS FOR THE REMOVAL OF ALCOHOLS

[75] Inventors: Wilhelm Johannisbauer, Erkrath; Hermann Koerner, Duesseldorf; Michael Nitsche, Solingen, all of Germany

[73] Assignee: Henkel Kommanditgesellschaft auf Aktien, Duesseldorf, Germany

[21] Appl. No.: 282,409

[22] Filed: Jul. 28, 1994

Related U.S. Application Data

[63] Continuation of Ser. No. 844,570, Mar. 27, 1992, abandoned.

[30] Foreign Application Priority Data

Sep. 27, 1989 [DE] Germany .......................... 39 32 173.8

[51] Int. Cl.[6] .................. C07H 1/06; C07H 15/04
[52] U.S. Cl. .................. 536/4.1; 536/18.5; 536/18.6; 536/124; 536/127
[58] Field of Search .................. 536/4.1, 18.5, 536/18.6, 124, 127

[56] References Cited

U.S. PATENT DOCUMENTS

| | | | |
|---|---|---|---|
| 4,143,072 | 3/1979 | Hetzel et al. | 536/120 |
| 4,380,625 | 4/1983 | Stadler et al. | 536/16.8 |
| 4,393,203 | 7/1983 | Mao et al. | 536/4.1 |
| 4,611,055 | 9/1986 | Yamamoto et al. | 536/127 |
| 4,684,720 | 8/1987 | Darsow et al. | 536/124 |
| 4,889,925 | 12/1989 | Schmid et al. | 536/18.6 |
| 4,977,285 | 12/1990 | Marquis et al. | 568/909.8 |
| 4,990,605 | 2/1991 | Lueders | 536/18.5 |
| 5,079,350 | 1/1992 | Fujita et al. | 536/18.5 |

FOREIGN PATENT DOCUMENTS

| | | |
|---|---|---|
| 0032252 | 7/1981 | European Pat. Off. . |
| 0092876 | 2/1983 | European Pat. Off. . |
| 3529983 | 3/1986 | Germany . |
| 3723826 | 1/1989 | Germany . |
| 3827534 | 2/1990 | Germany . |
| 3833780 | 4/1990 | Germany . |

*Primary Examiner*—Michael G. Wityshyn
*Assistant Examiner*—Everett White
*Attorney, Agent, or Firm*—Ernest G. Szoke; Wayne C. Jaeschke; Henry E. Millson, Jr.

[57] ABSTRACT

The invention relates to a process for the removal of alcohols containing up to 30 and, more particularly, between 8 and 18 carbon atoms by distillation from a mixture of alkyl glycosides and alcohols remaining unreacted in the production of these alkyl glycosides, the alcohols being removed in two stages, a falling-film evaporator being used in the first stage and a thin-layer evaporator being used in the second stage.

13 Claims, No Drawings

PROCESS FOR THE REMOVAL OF ALCOHOLS

This application is a continuation of application Ser. No. 07/844,570, filed on Mar. 27, 1992, now abandoned.

This invention relates to a process for the removal of alcohols containing up to 30 and, more particularly, between 8 and 18 carbon atoms by distillation from a mixture of alkyl glycosides and alcohols remaining unreacted in the production of these alkyl glycosides, the alcohols being removed in two stages.

Alkyl glycosides are reaction products of sugars of any type and aliphatic alcohols. The sugars may be monosaccharides, such as pentoses and hexoses, disaccharides, such as sucrose and maltose, and polysaccharides, such as starch. These carbohydrates are reacted with saturated or unsaturated aliphatic alcohols containing 1 to 30 carbon atoms and, more particularly, 8 to 18 carbon atoms in the presence of a suitable acidic catalyst. Mixtures of alkyl monoglycosides and alkyl polyglycosides or alkyl oligoglycosides, referred to hereinafter as alkyl glycosides, are obtained. The reaction is generally carried out with a large excess of alcohol, so that a mixture of alkyl glycosides and alcohols is obtained as the reaction product. Since the alcohols adversely affect the performance properties of the alkyl glycosides, they have to be removed from the alkyl glycosides. The alcohols removed are then best returned to the reactor for reasons of economy.

Since the boiling points of the alcohols are very high, particularly where fatty alcohols, i.e. alcohols containing 8 or more carbon atoms obtained primarily from industrial fats, are used, and since unreacted sugar residues decompose at temperatures above 150° C., undesirably turning dark in color in the process, the removal of the alcohols by distillation is carried out either with addition of entraining agents or in a fine vacuum (EP-PS 92 876). The addition of entraining agents has the disadvantages that the product comes into contact with additional substances which, on the one hand, can adversely affect product quality and which, on the other hand, necessitate increased expenditure on equipment for the removal and return of the entraining agent. Where distillation is carried out in the absence of entraining agents, thin-layer evaporators are used on account of the temperature sensitivity and on account of the high viscosity of the alkyl glycosides freed from the alcohol. Thin-layer evaporators are apparatus in which the starting mixture is applied to a heated wall where it is mechanically distributed by— generally rotating—wiping elements so that a very good heat exchange is obtained between wall and fluid and local overheating is avoided.

The distillation of the crude product in a single stage in a thin-layer evaporator is proposed in European patent 92 876. If the alcohol content in the alkyl glycoside has to be reduced to below 1% by weight, as is generally necessary for obtaining a product which dissolves clearly in water, the average load on the heating surface is very low so that a very large evaporator has to be used, making the process uneconomical.

Earlier German patent application P 38 33 780.0 describes a process of the type mentioned at the beginning in which the crude product is distilled in two stages in a combination of a thin layer evaporator and a short-path evaporator. Short-path evaporators are thin-layer evaporators with an internal condenser which are operated at evaporator pressures of $10^{-1}$ to $10^{-4}$ mbar. In view of the short distance between the heating surface and the condensation surface, the less readily volatile component is entrained in the event of delays in boiling so that more of that component enters the distillate. Entrainment of the product results both in a reduction in yield and in a deterioration in the quality of the distillate; the distillate contaminated with product cannot be returned to the reaction section without additional purification.

EP-PS 32 252, German patent application P 38 27 534.1 and DE-OS 37 23 826 Al are cited as further prior art.

The problem addressed by the present invention was to provide a process for separating mixtures of alkyl glycoside and alcohol by distillation which, for reasonable overall costs, would enable the alcohol content of the product to be reduced as required to values of 0.1 to 10% by weight and which, at the same time, would give a high-quality distillate substantially free from alkyl glycoside.

According to the invention, the solution to this problem in a process of the type mentioned at the beginning is characterized in that a falling-film evaporator is used in the first stage while a thin-layer evaporator is used in the second stage.

In one particular embodiment of the invention, the sump temperature of the falling-film evaporator is in the range from 100° to 220° C. and more particularly in the range from 140° to 180° C. In another embodiment, the falling film evaporator is operated at a pressure of 1 to 20 mbar and, more particularly, 3 to 10 mbar.

In the case of the thin-layer evaporator, a sump temperature of 120° to 250° C. and, more particularly, 160° to 230° C. is favorable. The operating pressure of the thin-layer evaporator should be in the range from 0.1 to 5 mbar and, more particularly, in the range from 0.5 to 1.5 mbar.

In another advantageous embodiment of the invention, the operating parameters of the falling-film evaporator are adjusted in such a way that alcohol contents of 10 to 50% by weight and, more particularly, 20 to 30% by weight are obtained at its outlet.

In another favorable embodiment, the falling-film evaporator is operated with external forced circulation.

Finally, the operating parameters of the thin-layer evaporator are adjusted in such a way that alcohol contents of 0.1 to 10% by weight and, more particularly, 0.3 to 3% by weight are obtained at its outlet.

Because the minimal alcohol concentration in the sump of the first stage is limited to 10% by weight, the viscosity of the mixture remains so low that it is possible to use a falling-film evaporator which is far less expensive than a thin-layer evaporator. To obtain an adequate peripheral load and hence to ensure complete wetting of the evaporator surface, it is advisable to operate the evaporator with external forced circulation. However, providing the geometry of the apparatus is suitably selected, the evaporator may also readily be operated on the basis of a single passage.

The use of a thin-layer evaporator as a second distillation stage largely avoids the entrainment of alkyl glycoside, so that distinctly less than 1% by weight alkyl glycoside is found in the distillate, as opposed to the 30% by weight alkyl glycoside found in the distillate of a short-path evaporator. The poorer vacuum compared with the short-path evaporator is compensated by a slight increase in the temperature of the heating medium. The increased exposure of the product to heat results in slightly poorer color quality of the untreated sump product. However, after the product dissolved in water has been chemically bleached, generally in a final step, there are no longer any discernible differences in color quality.

One example of embodiment of the invention is described in the following.

A mixture of alkyl glucoside and fatty alcohols was separated in a two-stage distillation plant consisting of a falling-film evaporator with an evaporator surface of 4.5 m² and a thin-layer evaporator with an evaporator surface of 1 m². The alkyl glucoside had been synthesized from potato starch and a mixture of lauric and myristic alcohol, the molar ratio of glycose to alcohol being 1:4.5. The falling film evaporator was operated with a heating medium temperature of 180° C., a sump temperature of 160° C. and a pressure of approx. 8 mbar. The thin-layer evaporator was operated with a heating medium temperature of 210° C., a sump temperature of 200° C. and a pressure of approximately 1 mbar. Under steady-state operating conditions, a stream of 300 kg/h reaction mixture with a fatty alcohol content of approx. 70% by weight was fed to the falling-film evaporator. In the first distillation stage, the fatty alcohol content was reduced to approx. 30% by weight, so that a stream of approx. 130 kg/h could be fed to the thin-layer evaporator. The sump product of the second distillation stage contained approx. 0.8% by weight residual fatty alcohol.

We claim:

1. In a process for the removal of alcohols containing from 8 to 30 carbon atoms from a mixture of alkyl glycosides and such alcohols, the improvement wherein the alcohols are removed from said mixture in two stages comprising the steps of a) passing said mixture through a falling-film evaporator to obtain partial removal of alcohols from the mixture, wherein the sump temperature is maintained in the range of from about 140° to about 220° C., and the pressure is maintained in the range of from about 1 to about 20 mbar, and b) passing the mixture from step a) through a thin-layer evaporator to remove further quantities of alcohols, wherein the sump temperature is in the range of from about 160° to about 250° C., and the pressure is maintained in the range of from about 0.1 to about 5 mbar.

2. The process of claim 1 wherein the alcohols contain from 8 to 18 carbon atoms.

3. The process of claim 1 wherein said temperature in step a) is in the range of from about 140° to about 180° C.

4. The process of claim 1 wherein said pressure in step a) is in the range of from about 3 to about 10 mbar.

5. The process of claim 1 wherein in step b) the sump temperature in the thin-layer evaporator is from about 160° to about 230° C.

6. The process of claim 1 wherein in step b) the operating pressure in the thin-layer evaporator is in the range of from about 0.5 to about 1.5 mbar.

7. The process of claim 1 wherein in step a) the operating conditions in the falling-film evaporator are maintained to provide an alcohol content in said mixture at the outlet of the falling-film evaporator of from about 10 to about 50% by weight of the mixture.

8. The process of claim 7 wherein the alcohol content in said mixture at the outlet of the falling-film evaporator is from about 20 to about 30% by weight.

9. The process of claim 1 wherein in step a) the falling-film evaporator is operated with external forced circulation.

10. The process of claim 1 wherein in step b) the operating conditions in the thin-layer evaporator are maintained to provide an alcohol content in said mixture at the outlet of the thin-layer evaporator of from about 0.1 to about 10% by weight of the mixture.

11. The process of claim 10 wherein the alcohol content of the mixture at the outlet of the thin-layer evaporator is from about 0.3 to about 3% by weight.

12. The process of claim 1 wherein in step a) the sump temperature in the falling-film evaporator is in the range of from about 140° to about 180° C. and the operating pressure is from about 3 to about 10 mbar, and in step b) the sump temperature in the thin-layer evaporator is from about 160° to about 230° C. and the operating pressure is from about 0.5 to about 1.5 mbar.

13. The process of claim 12 wherein in step a) the falling-film evaporator is operated with external forced circulation.

* * * * *